(12) United States Patent
Lehtinen et al.

(10) Patent No.: US 11,571,219 B2
(45) Date of Patent: Feb. 7, 2023

(54) HEMOSTASIS CLIP TWO STAGE DEPLOYMENT MECHANISM TO ELIMINATE SHED PARTS

(71) Applicant: Boston Scientific Scimed, Inc., Maple Grove, MN (US)

(72) Inventors: Laurie A. Lehtinen, Boylston, MA (US); Joseph W. King, Franklin, MA (US); Daniel Congdon, Hudson, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 392 days.

(21) Appl. No.: 16/947,195

(22) Filed: Jul. 22, 2020

(65) Prior Publication Data

US 2021/0022742 A1    Jan. 28, 2021

Related U.S. Application Data

(60) Provisional application No. 62/877,873, filed on Jul. 24, 2019.

(51) Int. Cl.
*A61B 17/122* (2006.01)
*A61B 17/00* (2006.01)
*A61B 17/10* (2006.01)

(52) U.S. Cl.
CPC ...... *A61B 17/122* (2013.01); *A61B 17/00234* (2013.01); *A61B 17/10* (2013.01);
(Continued)

(58) Field of Classification Search
CPC . A61B 17/00234; A61B 17/10; A61B 17/122; A61B 17/128; A61B 17/1285;
(Continued)

(56) References Cited

U.S. PATENT DOCUMENTS

| 5,520,701 A | * | 5/1996 | Lerch | A61B 17/1285 |
| | | | | 606/151 |
| 5,749,881 A | * | 5/1998 | Sackier | A61B 17/122 |
| | | | | 606/151 |

(Continued)

FOREIGN PATENT DOCUMENTS

| CN | 107115130 | 9/2017 |
| EP | 3 053 532 | 8/2016 |
| WO | 2018/173474 | 9/2018 |

*Primary Examiner* — Ryan J. Severson
(74) *Attorney, Agent, or Firm* — Fay Kaplun & Marcin, LLP

(57) ABSTRACT

A clipping device includes a clip including a capsule and a pair of clip arms, proximal ends of which are slidably received within the channel to move the clip arms between an open configuration and a closed configuration. Each of the pair of clip arms includes an elongated opening extending through the proximal ends thereof. A connector includes a central portion received between the proximal ends of the clip arms and a pin extending from the central portion receivable within the opening of each of the clip arms, the connector movable from an unlocked configuration, in which the pin is received within a distal portion of the elongated opening, to a locked configuration, in which the pin is received within a proximal portion of the elongated opening, when a predetermined force is applied thereto.

20 Claims, 8 Drawing Sheets

(52) U.S. Cl.
CPC ............... *A61B 2017/00296* (2013.01); *A61B 2017/00818* (2013.01)

(58) Field of Classification Search
CPC ........... A61B 2017/00296; A61B 2017/00818; A61B 2017/12004
See application file for complete search history.

(56) References Cited

U.S. PATENT DOCUMENTS

| | | | | |
|---|---|---|---|---|
| 6,386,496 | B1* | 5/2002 | Lai | E05C 19/022 248/222.12 |
| 7,452,327 | B2* | 11/2008 | Durgin | A61B 17/122 606/139 |
| 8,062,311 | B2* | 11/2011 | Litscher | A61B 17/1285 606/143 |
| 8,083,668 | B2* | 12/2011 | Durgin | A61B 17/083 606/139 |
| 8,685,048 | B2* | 4/2014 | Adams | A61B 17/1227 606/157 |
| 8,974,371 | B2* | 3/2015 | Durgin | A61B 17/122 606/139 |
| 9,005,219 | B2* | 4/2015 | Cohen | A61B 17/1227 606/151 |
| 9,370,371 | B2* | 6/2016 | Durgin | A61B 17/122 |
| 9,980,725 | B2* | 5/2018 | Durgin | A61B 34/76 |
| 10,143,479 | B2* | 12/2018 | Adams | A61B 17/1285 |
| 10,952,725 | B2* | 3/2021 | Durgin | A61B 17/1285 |
| 10,952,742 | B2* | 3/2021 | Lehtinen | A61B 17/122 |
| 11,045,194 | B2* | 6/2021 | King | A61B 17/128 |
| 11,071,552 | B2* | 7/2021 | Saenz Villalobos | A61B 17/1227 |
| 11,202,637 | B2* | 12/2021 | Murray | A61B 17/1285 |
| 11,395,661 | B2* | 7/2022 | Murray | A61B 17/1227 |
| 11,426,177 | B2* | 8/2022 | Congdon | A61B 17/1227 |
| 2005/0080440 | A1* | 4/2005 | Durgin | A61B 17/083 606/151 |
| 2005/0107809 | A1* | 5/2005 | Litscher | A61B 17/1285 606/142 |
| 2009/0043316 | A1* | 2/2009 | Durgin | A61B 17/083 600/106 |
| 2011/0046651 | A1* | 2/2011 | Cohen | A61B 17/1227 606/157 |
| 2012/0109162 | A1* | 5/2012 | Durgin | A61B 17/0682 606/142 |
| 2013/0006273 | A1* | 1/2013 | Adams | A61B 90/03 606/142 |
| 2013/0231685 | A1* | 9/2013 | Adams, Jr. | A61B 17/083 606/142 |
| 2014/0088616 | A1* | 3/2014 | Clerc | A61B 17/1285 606/142 |
| 2015/0173769 | A1 | 6/2015 | Durgin et al. | |
| 2015/0190136 | A1* | 7/2015 | Cohen | A61B 17/1227 606/143 |
| 2016/0213378 | A1* | 7/2016 | Adams | A61B 17/1227 |
| 2016/0242778 | A1 | 8/2016 | Xu et al. | |
| 2016/0262748 | A1* | 9/2016 | Durgin | A61B 17/083 |
| 2018/0153552 | A1* | 6/2018 | King | A61B 17/083 |
| 2018/0235608 | A1* | 8/2018 | Durgin | A61B 17/0682 |
| 2019/0159783 | A1* | 5/2019 | Lehtinen | A61B 17/122 |
| 2019/0231353 | A1* | 8/2019 | Saenz Villalobos | A61B 17/1285 |
| 2020/0155159 | A1* | 5/2020 | Murray | A61B 17/1285 |
| 2020/0375602 | A1* | 12/2020 | Congdon | A61B 17/1227 |
| 2021/0022742 | A1* | 1/2021 | Lehtinen | A61B 17/00234 |
| 2021/0022745 | A1* | 1/2021 | Murray | A61B 17/1285 |

\* cited by examiner

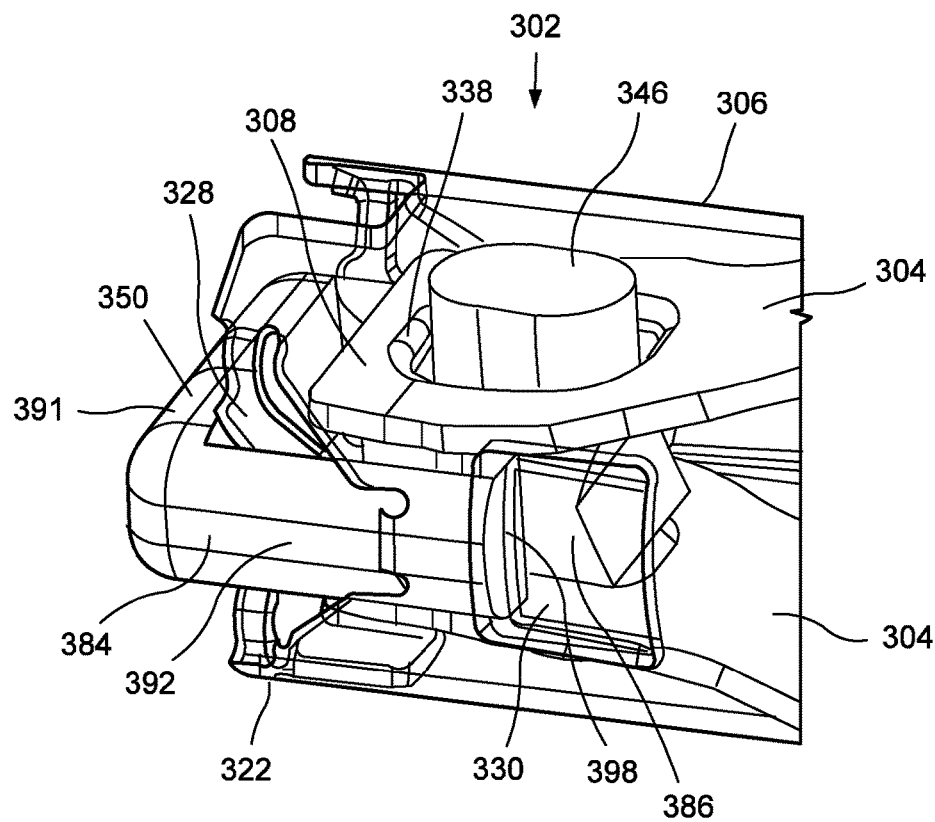
FIG. 13
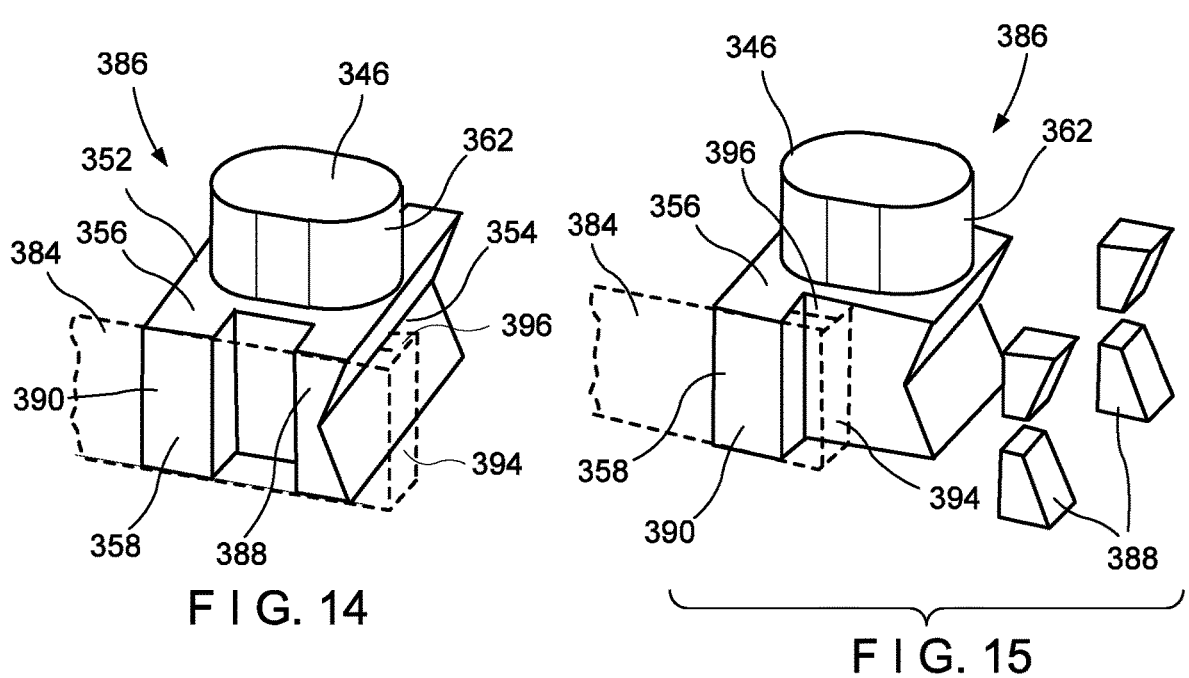
FIG. 14
FIG. 15

HEMOSTASIS CLIP TWO STAGE DEPLOYMENT MECHANISM TO ELIMINATE SHED PARTS

PRIORITY CLAIM

The present disclosure claims priority to U.S. Provisional Patent Application Ser. No. 62/877,873 filed Jul. 24, 2019; the disclosure of which is incorporated herewith by reference.

FIELD present disclosure relates to endoscopic devices and, in particular, relates to endoscopic clipping devices for treating tissue along the gastrointestinal tract.

BACKGROUND

During endoscopic gastrointestinal (GI) procedures, the patient may be at risk of perforation of a wall of the GI tract or may require closure of the GI tract wall as part of the procedure. Hemostasis clips may be used for hemostasis of, for example, mucosal/sub-mucosal defects, bleeding ulcers, arteries, polyps, diverticula, along with closure of luminal tract perforations. Depending on the size of the defect, multiple clips may be used.

SUMMARY

The present disclosure relates to a clipping device, comprising a clip including a capsule extending longitudinally from a proximal end to a distal end and including a channel extending therethrough, and a pair of clip arms, proximal ends of which are slidably received within the channel to move the clip arms between an open configuration and a closed configuration. Each of the pair of clip arms includes an elongated opening extending through the proximal ends thereof. A connector includes a central portion receivable between the proximal ends of the clip arms and a pin extending from the central portion receivable within the opening of each of the clip arms. The connector is movable from an unlocked configuration, in which the pin is received within a distal portion of the elongated opening, to a locked configuration, in which the pin is received within a proximal portion of the elongated opening, when a predetermined force is applied thereto. A control member extends through a proximal portion of the clipping device from a proximal end to a distal end releasably coupled to the connector so that a longitudinal movement of the control member relative to the capsule moves the clip between the open and the closed configurations, when the connector is in unlocked configuration.

In an embodiment, the capsule may include a locking tab biased to extend radially into the channel so that, when the pin is moved from the distal portion of the elongated opening to the proximal portion of the elongated opening, the pin is moved proximally past the locking tab until the pin engages the locking tab to lock the clip in the closed configuration.

In an embodiment, the distal and proximal portions of the elongated opening may be connected via a middle portion having a width smaller than a width of the distal and proximal portions so that one of the pin and a portion of the clip arms deforms to permit movement of the pin from the distal portion to the proximal portion.

In an embodiment, each of the clip arms may include a slit extending from a proximal-most end of the clip arms to the elongated opening to define a pair of fingers that deform by spreading relative to one another to permit movement of the pin proximally past the middle portion.

In an embodiment, the connector may include an overhang extending from the pin to engage an exterior surface of each of the clip arms.

In an embodiment, the central portion of the connector may be sized and shaped so that, when the connector is moved from the unlocked configuration to the locked configuration, the central portion moves inwardly crimped tabs at the proximal end of the capsule radially outward, releasing the clip from the proximal portion of the clipping device.

In an embodiment, the connector may be connected to the control member via one of a weld, crimped portion and ball tip of the control member that is configured to separate when a predetermined force greater than the predetermine force for moving the connector from the unlocked configuration to the locked configuration is applied thereto.

The present disclosure relates to a clipping device, comprising a clip including a capsule extending longitudinally from a proximal end to a distal end and including a channel extending therethrough, and a pair of clip arms, proximal ends of which are slidably received within the channel to move the clip arms between an open configuration and a closed configuration. Each of the pair of clip arms includes an opening extending through the proximal ends thereof. A connector includes a central portion receivable between the proximal ends of the clip arms and a pin extending from the central portion receivable within the opening of each of the clip arms. At least a portion of the central portion is configured to be movable relative to the pin and the clip arms from an unlocked configuration to a locked configuration, when a predetermined force is applied thereto. A control member extends through a proximal portion of the clipping device from a proximal end to a distal end releasably coupled to the connector so that a longitudinal movement of the control member relative to the capsule moves the clip between the open and the closed configurations, when the connector is in unlocked configuration.

In an embodiment, the capsule may include a locking tab biased to extend radially into the channel so that, when the central portion is moved from the unlocked configuration to the locked configuration, a portion of the central portion engages the locking tab to lock the clip in the closed configuration.

In an embodiment, the central portion may include an elongated opening extending therethrough, the pin received within the elongated opening and movable relative thereto from a proximal portion of the elongated opening in the unlocked configuration to a distal portion of the elongated opening in the locked configuration.

In an embodiment, the proximal and distal portions of the elongated opening may be connected to one another via a middle portion having a width smaller than a width of the proximal and distal portions of the elongated opening, so that the pin deformed to permit movement from the proximal portion to the distal portion of the elongated opening.

In an embodiment, the central portion may include an interior member from which the pin extends and a sliding member connected to the interior member via shear tabs that are configured to be sheared off when subject to the predetermined force to move the sliding member from the unlocked configuration to the locked configuration.

In an embodiment, the sliding member may include a pair of sliding arms extending along opposing sides of the interior member, inwardly extending fingers at distal ends of the sliding arms engaging shear tabs at a distal end of the interior member.

In an embodiment, the pin may engage the opening of each of the clip arms via one of a friction fit, a weld, an adhesive, and an overhang extending from the pin.

In an embodiment, the central portion of the connector may be sized and shaped so that, when the connector is moved from the unlocked configuration to the locked configuration, the central portion engages inwardly crimped tabs at the proximal end of the capsule to move the crimped tabs radially outward, releasing the clip from the proximal portion of the clipping device.

The present disclosure also relates to a method for clipping tissue. A clip device is inserted through a working channel of an endoscope to a target site within a body until a clip of the clip device extends distally past a distal end of the working channel. The clip device includes a capsule and a pair of clip arms slidably received therein. The clip device is moved between an open configuration and a closed configuration, using a control wire coupled to the clip arms until target tissue is received between the distal ends as desired. A distal end of the control wire is coupled to proximal ends of the clip arms via a connector including a central portion received between the proximal ends of the clip arms and a pin extending therefrom receivable within an elongated opening extending through proximal ends of each of the clip arms.

The clip arms are drawn proximally into the capsule to move the clip toward the closed configuration to grip the target tissue between the clip arms. The clip is locked in the closed configuration by drawing the control member proximally relative to the capsule until a predetermined force is exerted on the connector, moving the pin from a distal portion of the elongated opening to a proximal portion of the elongated opening so that the pin engages a locking tab biased radially into the channel of the capsule.

BRIEF DESCRIPTION

FIG. 13 shows an enlarged perspective view of a portion of the clipping device of FIG. 11, in a locked and deployed configuration;

FIG. 14 shows a perspective view of a portion of a connector according to the clipping device of FIG. 11; and FIG. 15 shows a perspective view of a portion of a connector according to the clipping device of FIG. 11, with shear tabs sheared off.

DETAILED DESCRIPTION

Figure 1A:
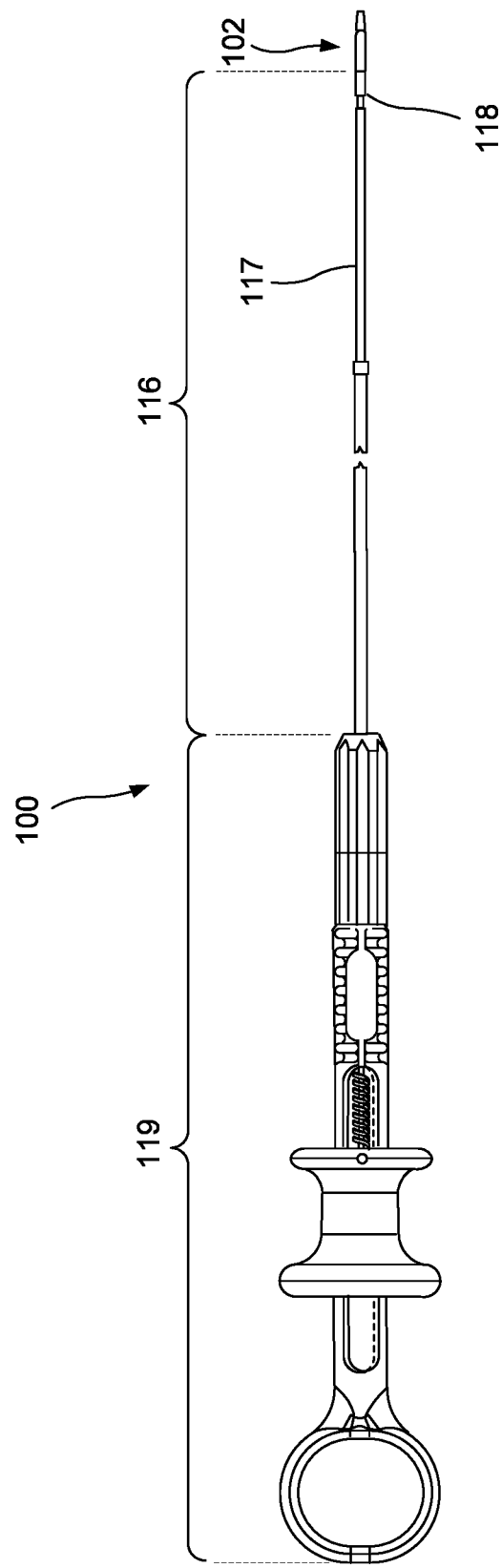
FIG. 1A shows a longitudinal side view of a clipping device according to an exemplary embodiment of the present disclosure.
Figure 1B:
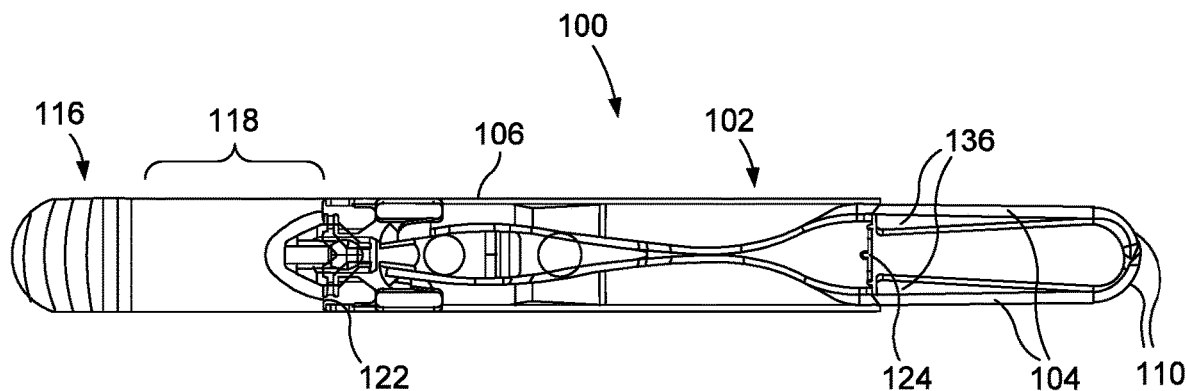
FIG. 1B shows a partially transparent longitudinal side view of a clip according to the device of FIG. 1A.

The present disclosure may be further understood with reference to the following description and the appended drawings, wherein like elements are referred to with the same reference numerals. The present disclosure is directed to an endoscopic clipping device for treating internal tissue perforations, defects and/or bleeds. In some cases, a shorter deployed clip may be preferred to improve visualization of the target site and to allow better maneuverability when placing multiple clips. In addition, although shed parts will pass naturally from the body under normal circumstances, shed parts may become trapped in larger defects after closure.

Exemplary embodiments of the present disclosure describe a clipping device comprising a clip including clip arms slidable within a capsule to move between an open configuration and a closed configuration to clip tissue, as desired. In particular, the clip arms are movable relative to the capsule via a control member including a connector at a distal end thereof for connecting the control member to the clip arms. The connector is coupled to a proximal end of the clip arms so that, once the clip is clipped over a target tissue as desired, at least a portion of the connector slides proximally relative to the clip arms to lock the clip arms relative to the capsule and facilitate a deployment of the clip from a proximal portion of the device. The sliding connector remains attached to the clip arms upon deployment. The sliding connector, including the locking mechanism thereof, reduces a potential length of the clip arms and/or shed parts of the clip in the body. It will be understood by those of skill in the art that the terms proximal and distal as used herein, are intended to refer to a direction toward and away from, respectively, a user of the device.

As shown in FIGS. 1A-7, a clipping device 100 comprises a clip 102 including a pair of clip arms 104, proximal ends 108 of which are slidably received within a capsule 106 so that the clip arms may move between an open configuration, in which distal ends 110 of the clip arms 104 are separated from one another, and a closed configuration, in which distal ends 110 are drawn toward one another. The clip arms 104 are moved between the open and the closed configurations via proximal and distal movement of a control member 112, which is coupled to the clip arms 104 via a connector 114. The connector 114 is configured to maintain an alignment between the clip arms 104, to lock the clip arms 104 relative to the capsule 106 once a target tissue has been clipped, and to facilitate deployment of the clip from a proximal portion 116 of the clipping device 100, which facilitates insertion of the clip 102 to a target site.

In some embodiments, once the clip 102 has been clipped over a target tissue, the control member 112 is drawn proximally relative to the capsule 106 until at least a portion of the connector 114 slides proximally relative to the clip arms 104 to, as will be described in further detail below, lock the clip 102 in the closed configuration and facilitate deployment of the clip 102 from the proximal portion 116. The proximal portion 116 may, for example, include a flexible elongate member 117 housing the control member 112 and connecting the clip 102 to a handle 119 and/or actuator(s) which, during use, remain outside the body accessible to a user to permit the user to control operation and movement of the device 100 between the open and closed configurations and to deploy the clip 102 over target tissue. The flexible elongate member may be releasably coupled to the clip 102 via a bushing 118 at a distal end of the flexible elongate member. The control member 112 extends through the elongate member from a proximal end connected to a portion of the handle member to a distal end 120 connected to the connector 114.

The capsule 106 extends from a proximal end 122 to a distal end 124 and includes a channel 126 extending therethrough. In one embodiment, the proximal end 122 is configured to be releasably coupled to the bushing 118 via, for example, tabs 128 that are crimped radially inward to engage a corresponding portion of the bushing 118. A proximal portion of the capsule 106 also includes locking tabs 130 extending into the channel 126. In one example, the locking tabs 130 are defined via a cut portion of a wall 132 of the capsule 106 that is angled or bent into the channel 126 so that a proximal end 134 of the locking tab 130 is biased toward a centerline of the capsule 106.

Each of the clip arms 104 extends from the proximal end 108 to the distal end 110. As described above, proximal portions of the clip arms 104 are slidably received within the channel 126 of the capsule 106. Specifically, the proximal end 108 of each of the clip arms 104 is slidably received within the channel 126 allowing the clip 102 to be moved between the open and closed configurations via manipulation of the control member 112. In one embodiment, the clip arms 104 are biased toward the open configuration so that, when advanced distally out of the capsule 106, the clip arms 104 moved apart from one another into the open configuration under their natural bias. When the arms 104 are drawn proximally into the capsule 106, the clip arms 104 are constrained by the wall 132 of the capsule 106 and drawn together toward the closed position in which the distal ends 110 are adjacent one another. Those skilled in the art will understand that any number of other mechanisms for opening and closing the clip arms 104 may be employed.

The clip arms 104 of this embodiment also include engaging features 136 extending therefrom and configured to engage a portion of the capsule 106 so that, when the engaging features 136 engage the capsule 106, the clip arms 104 are prevented from being moved further proximally into the capsule 106. In one embodiment, the engaging features 136 extend laterally outward having a greater width than more proximal portions of the clip arms 104 that are sized to permit them to be drawn proximally into the capsule 106. Thus, as the clip arms 104 are drawn proximally into the capsule 106, the engaging features 136 abut the distal end 124 of the capsule 106. The engaging features 136 are positioned along the clip arms 104 so that, at the point where the engaging features 136 have engaged the capsule 106, the clip arms 104 have been drawn sufficiently proximally into the capsule 106 to draw the clip arms 104 together into the closed configuration. In one example, the engaging features 136 are configured as wings extending laterally from longitudinal edges of the clip arms 104.

Proximal ends 108 of the clip arms 104 include an elongated opening 138 extending therethrough for receiving a portion of the connector 114 therein. The elongated opening 138 includes a proximal portion 140 and a distal portion 142 connected to one another via a middle portion 144 having a width smaller than a width (e.g., diameter) of each of the proximal and distal portions 140, 142. Each of the proximal and distal portions 140, 142 are sized and shaped to receive a portion of the connector 114 such as, for example, a pin 146, therein.

Figure 2:
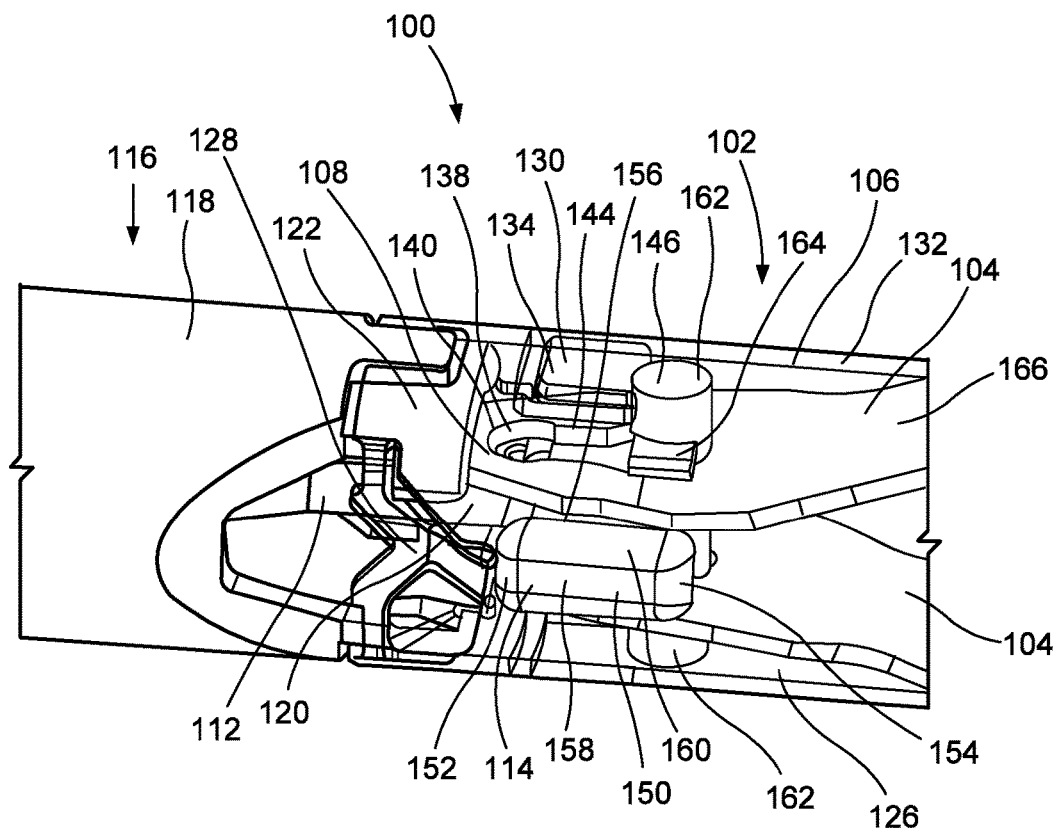
FIG. 2 shows an enlarged perspective view of a portion of the clipping device of FIG. 1A, in a closed, undeployed configuration.

In an unlocked configuration, in which the clip arms 104 are movable with respect to the capsule 106, the pin 146 is received within the distal portion 142 of the elongated opening 138 (see e.g., FIG. 2). In a locked configuration, in which the clip arms 104 are locked relative to the capsule 106 in the closed configuration, the pin 146 is received within the proximal portion 140 of the elongated opening 138 (see e.g., FIG. 3). The width of the middle portion 144 is smaller than the widths of the proximal and distal portions 140, 142 so that the pin 146 is prevented from inadvertently sliding from the distal portion 142 to the proximal portion 140 until it is desired to lock the clip 102 in the closed configuration. In some embodiments, the pin 146 is configured to move from the distal portion 142 to the proximal portion 140 when a predetermined force is applied thereto via the control member 112.

Figure 5:
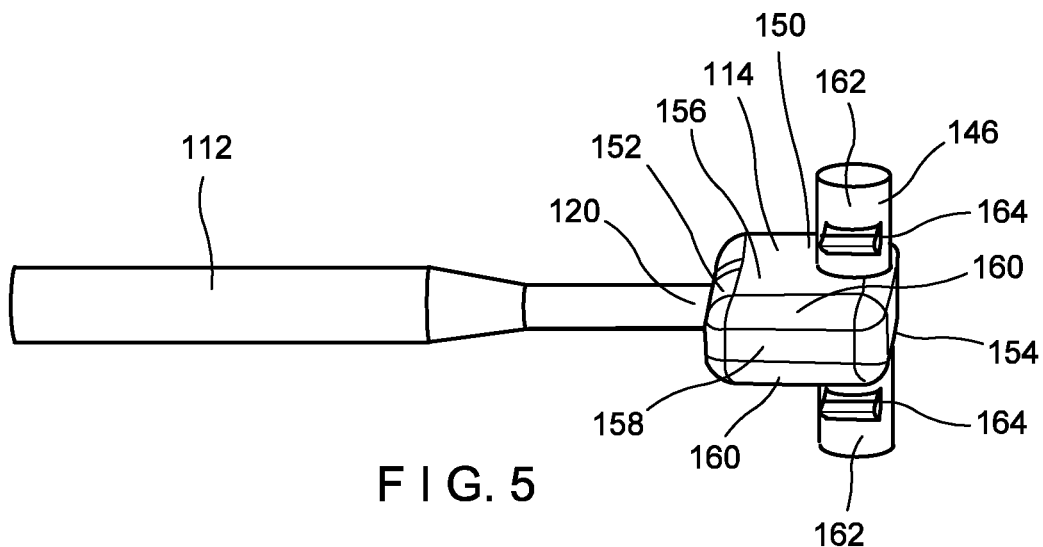
FIG. 5 shows a perspective view of a control member and a connector according to the clipping device of FIG. 1A.

As discussed above, the control member 112 is connected to the clip arms 104 via the connector 114, so that a movement of the control member 112 controls a movement of the clip 102 and, in particular, a movement of the clip arms 104 relative to the capsule 106. As shown in FIG. 5, the connector 114 is releasably attached to a distal end 120 of the control member 112 and includes a central portion 150 that is sized and shaped to be received between the proximal ends 108 of the clip arms 104 and the pin 146 which extends from opposing sides of the central body 150 to be received within the elongated opening 138. The central portion 150 extends from a proximal end 152 connected to the control member 112 to a distal end 154.

In one embodiment, the central portion is defined via opposing surfaces 156, each of which contacts a corresponding one of the clip arms 104, and lateral surfaces 158 connecting longitudinal edges 160 of the opposing surfaces 156. A distance between the lateral surfaces 158 is selected so that, when the connector 114 is slid proximally relative to the clip arms 104 from the unlocked to the locked configuration, the lateral surfaces 158 engage the inwardly crimped tabs 128 at the proximal end 122 of the capsule 106, moving the tabs 128 radially outward out of engagement with the bushing 118 of the proximal portion 116 of the device 100 to deploy the clip 102. In one embodiment, the distance between the lateral surfaces 158 substantially corresponds to a width (e.g., diameter) of the channel 126 of the capsule 106 so that the connector 114 is longitudinally slidable therewithin.

The pin 146 includes a protrusion 162 extending from each of the opposing surfaces 156 to be received within the elongated opening 138 of a corresponding one of the clip arms 104. In one embodiment, the pin 146 may include an overhang 164 extending laterally from each protrusion 162 so that when each protrusion 162 is received within the elongated opening 138 of the corresponding clip arm 104, the overhang 164 engages an exterior surface 166 of the clip arm 104 (e.g., a surface of the clip arm 104 facing away from the centerline of the capsule 106) to space the clip arm 104 from the channel 106 to prevent any friction that may occur from a sliding of the exterior surface 166 of the clip arm 104 against a surface of the channel 126.

As described above, the pin 146 moves from the unlocked configuration to the locked configuration when the engaging features 136 of the clip arms 104 engage the distal end 124 of the capsule 106 preventing further proximal movement of the clip arms 104 relative to the capsule 106. Thus, when the control member 112 is moved even further proximally relative to the capsule 106 so that a predetermined force is applied to the connector 114, the pin 146 moves from the distal portion 142 of the elongated opening 138 to the proximal portion 140 of the elongated opening 138 of the clip arms 104 via a middle portion 144 having a smaller width than the proximal and distal portions 140, 142 and the pin 146. In one example, one of the protrusions 162 of the pin 146 and/or portions of the clip arms 104 extending along either side of the middle portion 144 deform to permit the pin 146 to be moved proximally therepast.

Figure 4:
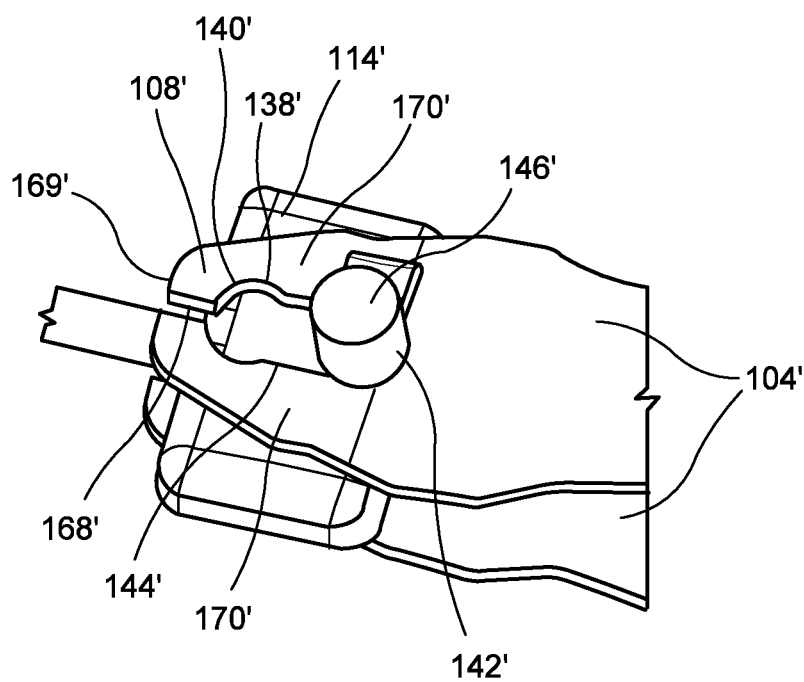
FIG. 4 shows a perspective view of a connector connected to clip arms of a clipping device according to an alternate embodiment.

In another example, as shown in FIG. 4, a proximal end 108' of clip arms 104' includes a slit 168' from a proximal-most end 169' end of the clip arms 104' to an elongated opening 138' to define a pair of fingers 170'. When a predetermined force is applied to a connector 114', which is substantially similar to the connector 114 described above, to move the connector 114' from an unlocked configuration to a locked configuration, the pair of fingers 170' flex or spread apart from one another to facilitate moving of a pin 146' of the connector 114' from a distal portion 142' of the elongated opening 138' to a proximal portion 140' of the elongated opening 138' via a middle portion 144' having a smaller width than the proximal and distal portions 140', 142'. Once the pin 146' is received within the proximal portion 140' of the elongated opening 138', however, the fingers 170' revert to their initial configuration so that the pin 146' is held within the proximal portion 140' and the clip arms 104' are locked relative to the capsule 106 via the locking tabs 130, as described above.

Figure 3:
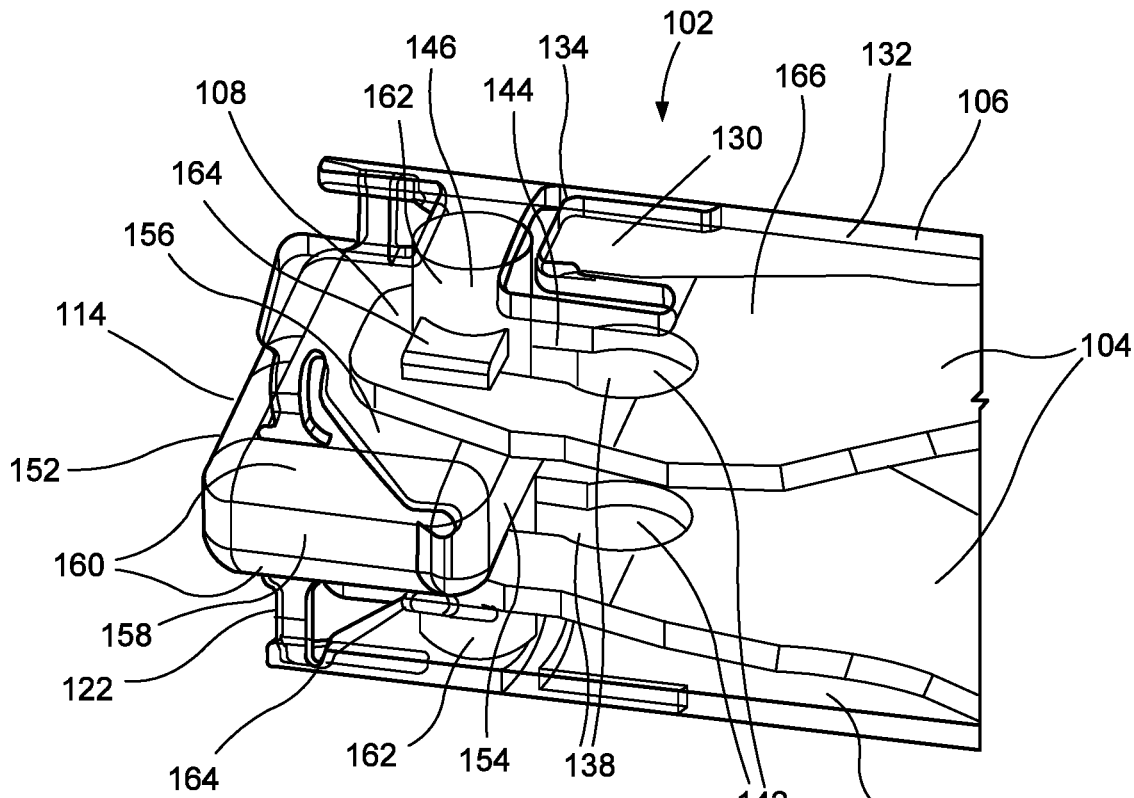
FIG. 3 shows an enlarged perspective view of a portion of the clipping device of FIG. 1A, in a locked and deployed configuration.

As shown in FIG. 3, the pin 146 extends across a width (e.g., diameter) of the channel 126 of the capsule 106 so that a length of the pin 146 substantially corresponds thereto. Thus, as the connector 114 is moved from the unlocked to the locked configuration, the pin 146 slides along the locking tabs 130 moving the locking tabs 130 radially outward as it moved proximally therepast. Once the pin 146 has been proximally beyond the locking tab 130, however, the locking tab 130 is permitted to revert to its angled/bent configuration so that the proximal end 134 thereof extends toward the centerline of the capsule 106. In the locked configuration, the pin 146 is proximal of the proximal end 134 of the locking tab 130 so that the pin 146 engages the locking tab 130 and is prevented from moving distally therepast, thereby locking the clip arms 104 relative thereto, in the closed configuration.

As described above, the connector 114 is releasably coupled to the distal end 120 of the control member 112. Thus, once the connector 114 has been moved to the locked configuration so that the central portion 150 moves the crimped tabs 128 out of engagement with the bushing 118 and the pin 146 is positioned within the proximal portion 140 of the opening 138, the control member 112 is moved even further proximally relative to the capsule 106 until a predetermined force is exerted thereon, releasing or otherwise separating the control member 112 from the connector 114. It will be understood by those of skill in the art that the predetermined force required to separate the control member 112 from the connector 114 is greater than the predetermined force required to move the connector 114 from the unlocked configuration to the locked configuration. Separation of the control member 112 from the connector 114 allows the proximal portion 116 to be removed from the body while leaving the clip 102 clipped over the target tissue within body.

Figure 6:
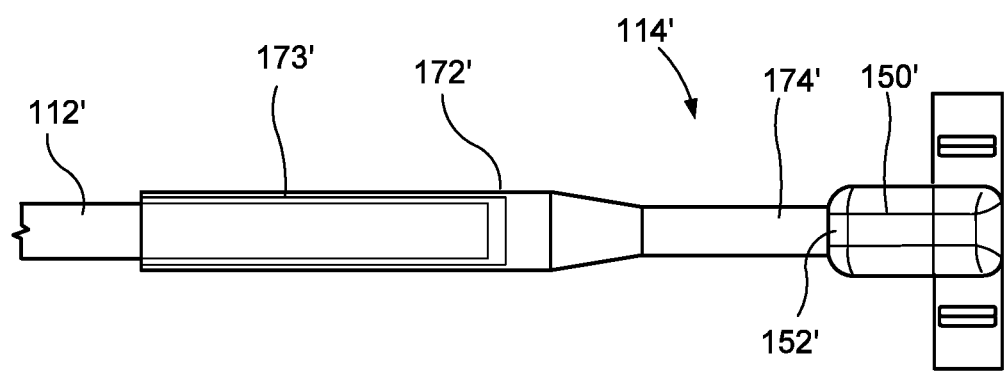
FIG. 6 shows a longitudinal side view of a control member and a connector according to an alternate embodiment.

It will be understood by those of skill in the art that the control member 112 may be releasably coupled to the connector 114 in any of a variety of ways. In one embodiment, as shown in FIG. 5, for example, the distal end 120 of the control member 112 may be welded to the proximal end 152 of the central portion 150 and configured to break or separate when the predetermined force is exerted thereon. In another example, as shown in FIG. 6, a connector 114' may include a sleeve 172' extending proximally from a proximal end 152' of a central portion 150' to be crimped over a distal portion of a control member 112'. Distally of a crimped portion 173' of the sleeve 172', the sleeve 172' includes a necked down portion 174' configured to fracture or break when the predetermined force is exerted thereon.

Figure 7:
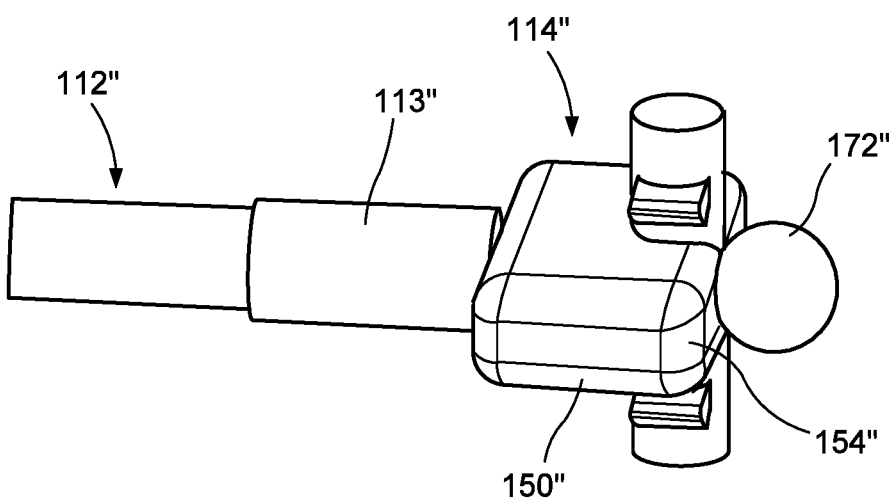
FIG. 7 shows a perspective view of a control member and a connector according to another alternate embodiment.

According to yet another example, as shown in FIG. 7, a control member 112" may include a ball tip 172" releasably coupled to a distal end 120" of the control member 112". In particular, a distal portion of the control member 112" extends through a central portion 150" of the connector 114" so that the ball tip 172' is distal of a distal end 154" of the central portion 150". Immediately proximal of the central portion 150" of the connector 114", a hypotube 113" may be crimped or welded over the control member 112" to prevent the control member 112" from sliding distally through the central portion 150" during opening of the clip 102. When a predetermined force is exerted thereon, the ball tip 172' separates from a remaining portion of the control member 112" so that the control member 112" may be proximally withdrawn from the central portion 150".

Although FIG. 7 specifically shows and describes a hypotube 113", it will be understood by those of skill in the art that the control member 112" may include other elements or mechanisms for preventing the distal movement of the control member 112" relative to the connector 114". For example, the control member 112" may alternatively include an increased diameter portion immediately distal of the central portion 150". Although specific examples are shown and described above, it will be understood by those of skill in the art that the control member 112 may be releasably coupled to the connector 114 in any of a number of ways so long as the control member 112 is releasable from the connector 114 when subject to a predetermined force.

According to an exemplary method utilizing the clipping device 100, the clip 102 inserted through, for example, a working channel of an endoscope to a target site within a body while the handle member remains exterior to the body. The clip 102 is inserted through the working channel in the closed configuration. Once the clip 102 has reached the target site, the user advances the control member 112 distally to advance the clip arms 104 distally out of the capsule 106 freeing the clip arms 104 to move under their natural bias toward the open configuration so that the target tissue may be received between the clip arms 104. The user may then operate the control member 112 to move the clip 102 between the open and closed configurations as desired until a target portion of tissue is positioned between the clip arms 104 as desired.

As described above, the clip arms 104 may be moved between the open and the closed positions while the control connector 114 is in the unlocked configuration with respect to the clip arms 104. In particular, the pin 146 of the connector 114 is received within the distal portion 142 of the elongated opening 138 extending through the proximal end of the clip arms 104. Once the target tissue has been clipped, as desired, the user draws the control member 112 proximally (or advances the proximal portion 116 distally over the control member 112) so that, as the clip arms 104 are drawn into the capsule 106, the clip arms 104 are drawn toward one another to grip the target tissue between the distal ends 110 of the clip arms 104.

When the clip 102 is in a desired position gripping the target tissue, the user applies increasing proximally directed force to the control member 112 after the engaging features 136 have engaged the capsule 106, as described above, until the pin 146 of the connector 114 moves proximally within the elongated opening 138 from the distal portion 142 thereof to the proximal portion 140 via the middle portion 144. As described above, either the clip 104 and/or the pin 146 may deform to permit proximal movement of the pin 146 through the middle portion 144, which has a smaller width than the proximal and distal portions 140, 142.

When the connector 114 is moved from the unlocked to the locked position, the pin 146 moves distally past the proximal end 134 of the locking tab 130 of the capsule 106 to lock the clip arms 104 relative to the capsule in the closed configuration, while also moving the inwardly crimped tabs 128 at the proximal end 122 of the capsule 106 radially outward via the lateral surfaces 158 of the central portion 150 to disengage the capsule 106 from the bushing 118. Once the connector 114 has been moved to the locked configuration, a proximal force on the control member 112 may be increased until the control member 112 separates from the connector 114, freeing the clip 102 from the proximal portion 116 of the device 100 and leaving the clip 102 coupled to the target tissue. The proximal portion 116, including the control member 112, may then be withdrawn from the body.

Figure 8:
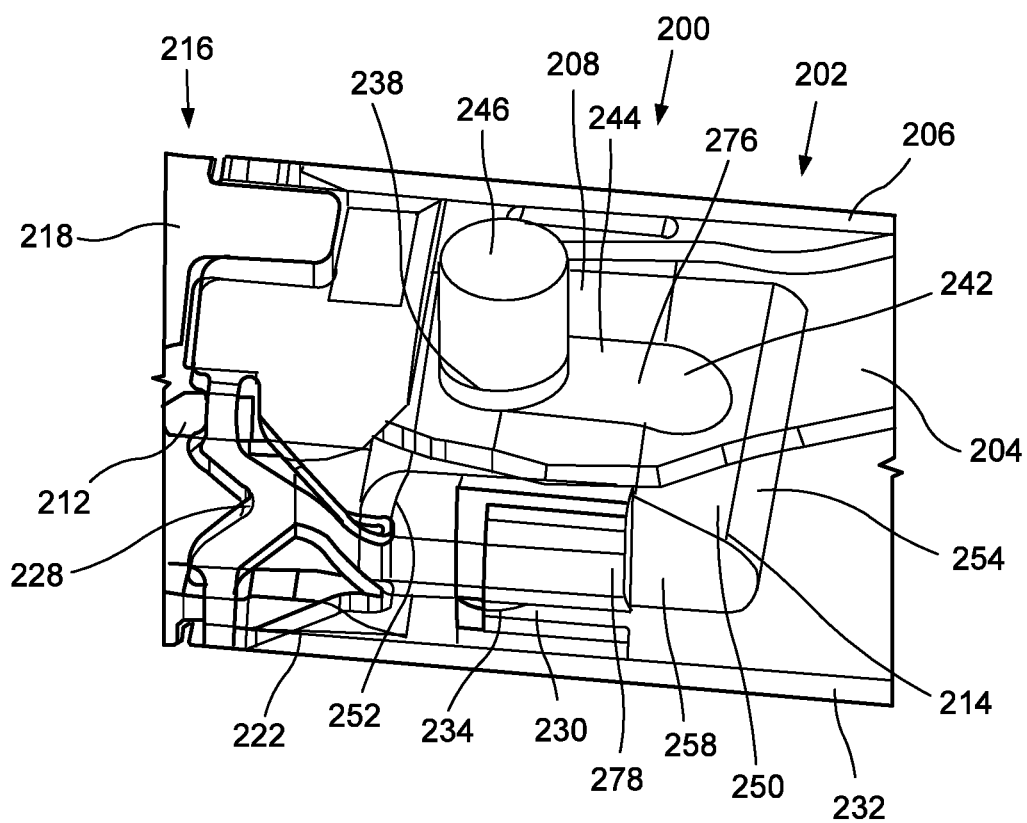
FIG. 8 shows an enlarged perspective view of a portion of a clipping device, in a closed, undeployed configuration, according to another exemplary embodiment of the present disclosure.
Figure 9:
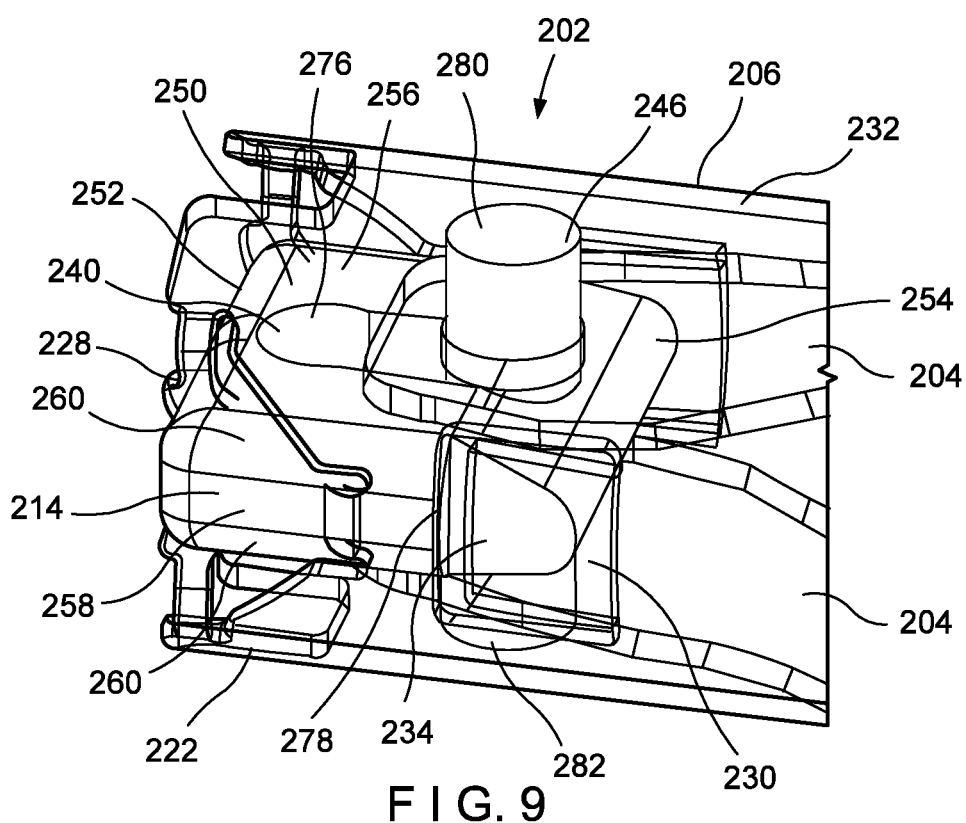
FIG. 9 shows an enlarged perspective view of a portion of the clipping device, in a locked configuration.
Figure 10:
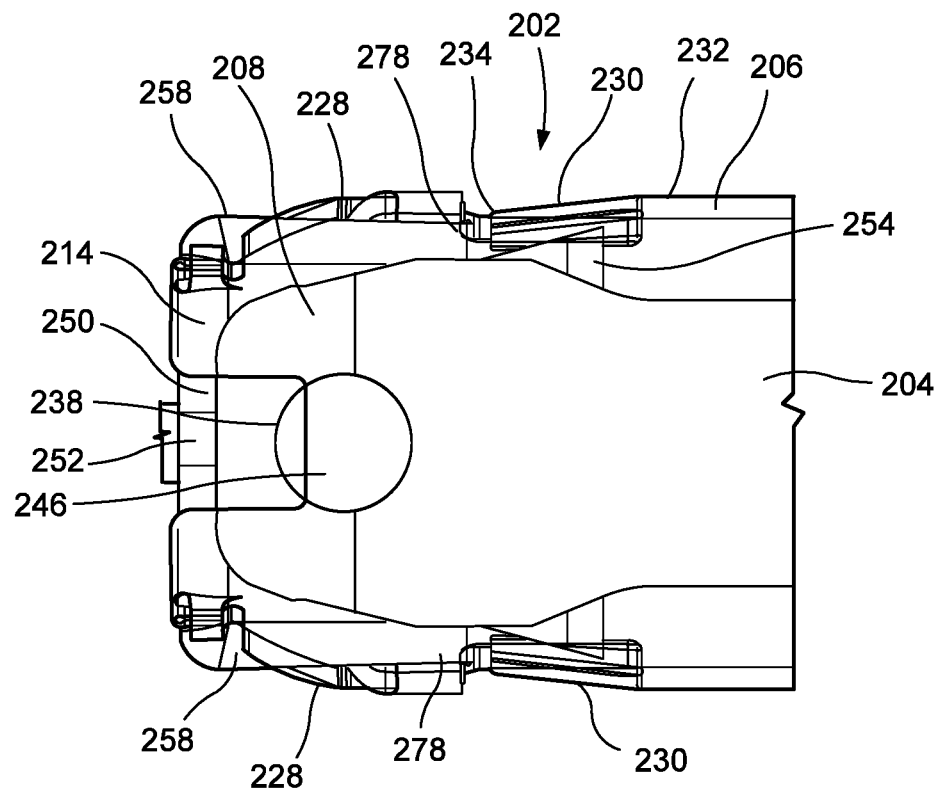
FIG. 10 shows a side view of a portion of the clipping device, in a locked and deployed configuration.

As shown in FIGS. 8-10, a clipping device 200 according to another exemplary embodiment is substantially similar to the clipping device 100 described above, and comprises a clip 202 including a pair of clip arms 204, proximal ends 208 of which are slidably received within a capsule 206 so that the clip 202 may move between an open configuration, in which distal ends of the clip arms 204 are separated from one another, and a closed configuration, in which distal ends are drawn toward one another. The clip arms 204 are moved between the open and the closed configurations via distal and proximal motion of a control member 212, which is coupled to the clip arms 204 via a connector 214. The connector 214 is substantially similar to the connector 114, including a central portion 250 and a pin 246. Rather than having the entire connector 214 moving proximally relative to the clip arms 204 to move the clip 202 from an unlocked to a locked configuration, however, the pin 246 remains in a fixed position relative to the clip arms 204 so that central portion 250 slides proximally relative to the pin 246 and the clip arms 204 to move the clip 202 from the unlocked to the locked configuration, as will be described in further detail below.

Similarly to the device 100, the connector 214 is releasably coupled to the control member 212 and includes the central portion 250 and the pin 246. The pin 246 extends from opposing surfaces of the central portion 250 to be received within openings 238 extending through proximal ends 208 of the clip arms 204. The opening 238, however, are not elongated, but rather, are specifically sized and shaped to correspond to a size and shape of the pin 246 received therein so that the pin 246 remains in a fixed position relative to the clip arms 204. In one embodiment, the pin 246 may be fixed to the openings 238 via a friction fit. In another embodiment, the pin 246 may be fixed to the openings 238 via, for example, welding or an adhesive. Alternatively, the pin 246 may include overhangs substantially similar to the overhangs 164 described with respect to the clipping device 100 for engaging the clip arms 204. Except as described above, the clip arms 204 are otherwise substantially similar to the clip arms 104.

The central portion 250 extends from a proximal end 252 to a distal end 254 and similarly to the central portion 150, is defined via opposing surfaces 256, each of which contact an interior surface of a corresponding one of the clip arms 204, and lateral surfaces 258 connecting longitudinal edges 260 of the opposing surfaces from the proximal end 252 to the distal end 254. The central portion 250 additionally includes, however, an elongated opening 276 extending therethrough from a first one of the opposing surfaces 256 to a second one of the opposing surfaces 256. The elongated opening 276 may be configured substantially similarly to the elongated opening 138 extending through the clip arms 104 of the clipping device 100. In particular, the elongated opening 276 may include a proximal portion 240 and a distal portion 242 connected to one another via a middle portion having a width smaller than the proximal and distal portions 240, 242. The pin 246, which will be described in further detail below, extends through the elongated opening 276. The pin 246 is received within the proximal portion 240 in the unlocked configuration (see FIG. 8) and is moved into the distal portion 242 in the locked configuration (see FIG. 9).

Similarly to the central portion 150, a distance between lateral surfaces 258 of the central portion 250 is selected so that, when the connector 214 is slid proximally relative to the pin 246 from the unlocked to the locked configuration, the lateral surfaces 258 engage inwardly crimped tabs 228 at a proximal end 222 of the capsule 206, moving the tabs 228 radially outward and out of engagement with a bushing 218 of a proximal portion 216 of the device 200 to deploy the clip 202. The lateral surfaces 258, however, further include a shoulder 278 for engaging locking tabs 230 of the capsule 206 in the locked configuration. Similarly to the locking tabs 130, locking tabs 230 may extend from a wall 232 of the capsule 206 to be angled or bent into a channel 226 of the capsule 206 so that a proximal end 234 of the locking tab 230 is biased toward a centerline of the capsule 206.

Since the pin 246 of the connector 214 remains fixed with respect to the clip arms 204, however, the locking tabs 230 engage the shoulder 278 of the central portion 250 when the central portion 250 is moved toward the locked configuration. In particular, as shown in FIG. 8, when the connector 214 is in the unlocked configuration, the central portion 250 is positioned between the locking tabs 230 so that the locking tabs 230 are deformed radially outward. When the central portion 250 is moved proximally relative to the pin 246 so that the pin 246 is received within the distal portion 242 of the elongated opening 276, however, the shoulder 278 is moved proximally past the locking tabs 230 so that the locking tabs 230 are permitted to revert to their inwardly biased configuration, as shown in FIGS. 9 and 10. The locking tabs 230 thus engage the shoulder 278 so that the central portion 250 can no longer be moved distally relative to the capsule 206, thereby locking the clip arms 204 relative to the capsule 206 in the closed configuration.

The pin 246 extends from a first end 280 to a second end 282 transverse relative to a longitudinal axis of the capsule so that the first end 280 is received within the opening 238 of a first one of the clip arms 204 and the second end 282 is received within the opening 238 of a second one of the clip arms 204. As described above, the pin 246 is received within the elongated opening 276 of the central portion 250 and is movable from the proximal portion 240 to the distal portion 242 as the clip 202 is moved from the unlocked configuration to the locked configuration. Similarly to the pin 146, the pin 246 may deform when subject to a predetermined force to pass through the middle portion 244, which has a smaller width than the proximal and distal portions 240, 242.

Figure 11:
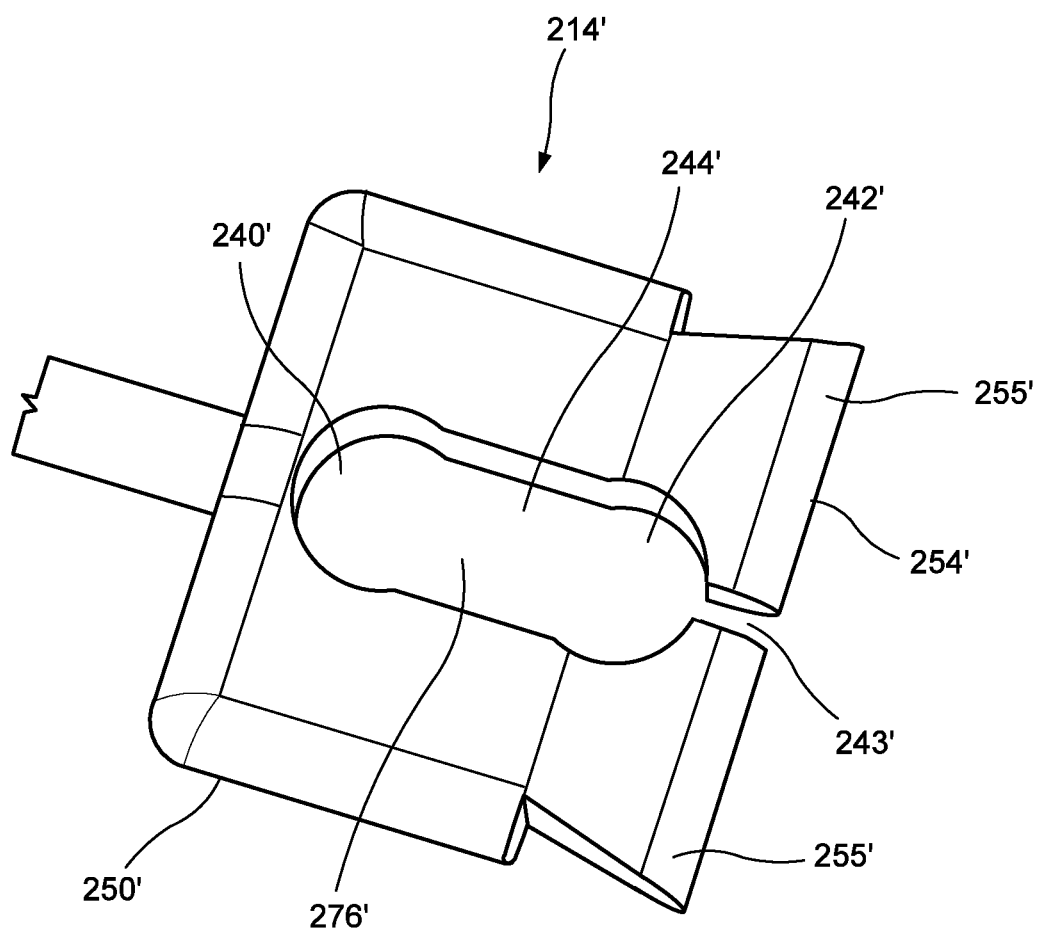
FIG. 11 shows a perspective view of an alternate embodiment of a connector according to the clipping device of FIG. 8.

According to an alternative embodiment, as shown in FIG. 11, a central portion 250' of a connector 214' may similarly include an elongated opening 276' through which a pin (substantially similarly to the pin 246) may be received. Similarly to the connector 214, the elongated opening 276' includes proximal and distal portions 240',242' connected to one another via a middle portion 244' having a smaller width than the proximal and distal portions 242', 242'. The central portion 250', however, further includes a slot 243' extending therethrough from the distal portion 242' to a distal end 254' such that the pin is not required to deform when passing through the middle portion 244'. In particular, when a predetermined load is applied to the connector 214', opposing portions 255' of the central portion 250' defined via the slot 243' spread apart from one another to permit the pin to move from the proximal portion 240' to the distal portion 242'. Once the pin is received within the distal portion 242', the central portion 250' reverts to its initial configuration to hold the pin within the distal portion 242'.

Except as outlined above, elements of the clipping device 200 may be substantially similar to the corresponding elements of the clipping device 100 so that, as will be understood by those of skill in the art, the clipping device 200 may be utilized in a manner substantially similar to the clipping device 100.

As shown in FIGS. 12-15, a clipping device 300 according to another exemplary embodiment of the present disclosure is substantially similar to the clipping devices 100, 200, except as described below. Similarly to the clipping devices 100, 200, the clipping device 300 comprises a clip 302 including a pair of clip arms 304, proximal ends 308 of which are slidably received within a capsule 306 so that the clip 302 may move between an open configuration, in which distal ends of the clip arms 304 are separated from one another, and a closed configuration, in which distal ends are drawn toward one another. The clip arms 304 are moved between the open and closed configurations via distal and proximal motion of a control member 312, which is coupled to the clip arms 304 via a connector 314.

Figure 12:
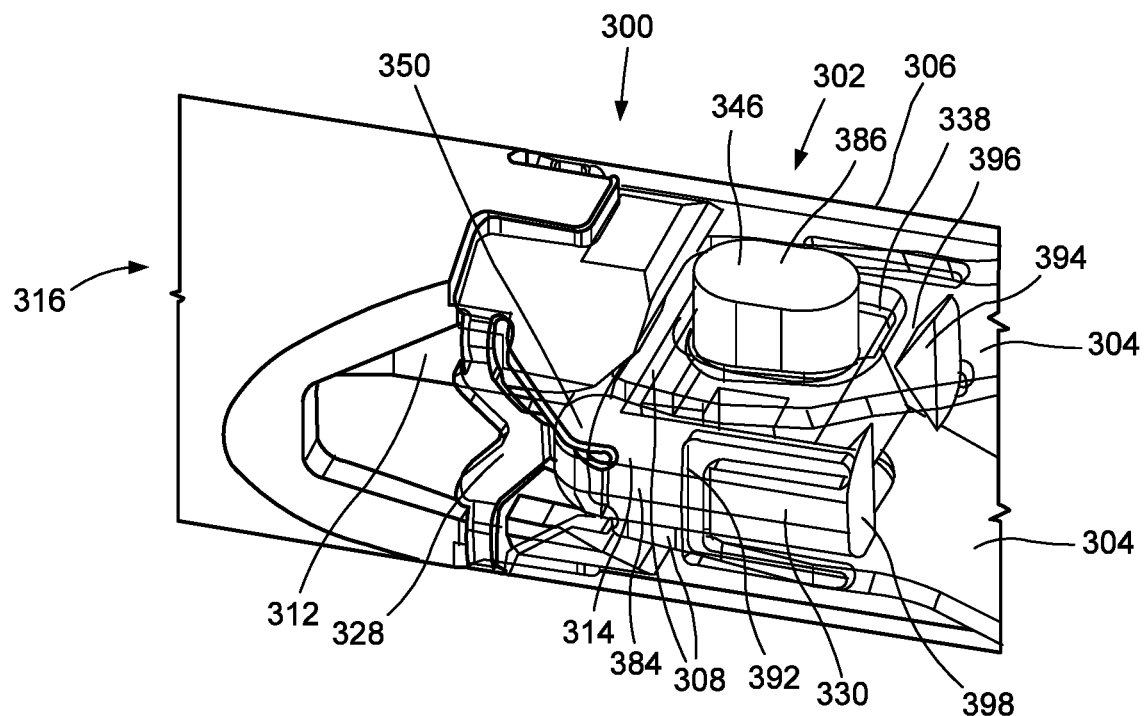
FIG. 12 shows an enlarged perspective view of a portion of a clipping device, in a closed, undeployed configuration, according to another exemplary embodiment of the present disclosure.

The connector 314 may be substantially similar to the connector 214 including a central portion 350 that is movable with respect to a pin 346 when moving the clip 302 from an unlocked configuration, as shown in FIG. 12, to a locked configuration, as shown in FIG. 13. The central portion 350, however, further includes a sliding member 384 extending about an interior component 386 so that, as will be described in further detail below, only the sliding member 384 is moved with respect to the pin 346 when the clip 302 is moved from the unlocked to the locked configuration.

The interior component 386 is sized and shaped to be received between the proximal ends 308 of the clip arms 304 and includes the pin 346 extending therefrom. Similarly to the pins 146, the pin 346 includes a pair of protrusions 362, each of the protrusions 362 extending from an opposing surface 356 of the interior component 386 to be received within an opening 338 extending through a corresponding one of the clip arms 304. Similarly to the clip 202, the opening 338 of clip 302 is specifically sized and shaped to correspond to the size and shape of the pin 346 received therein so that the pin 346 is in a fixed position relative thereto. Each of the opposing surfaces 356 contact an interior surface along the proximal end 308 of a corresponding one the clip arms 304.

As shown in FIG. 14, the interior component 386 also includes shear tabs 388 extending laterally from a distal end 354 thereof along with stop shoulders 390 extending from a proximal end 352 thereof. The shear tabs 388 are configured to be sheared off via a portion of the sliding component 384, when the clip 302 is moved from the unlocked to the locked configuration. The stop shoulders 390 are configured to abut a portion of the sliding component 384 to prevent the sliding component 384 from moving further proximally relative thereto and thereby preventing the sliding component 384 from becoming disengaged from the interior component 386. When the sliding component 384 abuts the stop shoulders 390, the clip 302 is in the locked configuration.

The sliding component 384 includes a proximal end 391 releasably coupled to the control member 312 and a pair of sliding arms 392 extending distally from the proximal end 391 to be mounted over the interior component 386 so that the pair of sliding arms 392 extend along the lateral sides 358 of the interior component 386. Each of the pair of sliding arms 392 include a radially inwardly extending finger 394 at a distal end 398 thereof which, in the unlocked configuration, engages the shear tabs 388 by extending distally thereover. In an embodiment, each finger 394 may include a cutting edge 396 so that, when the clip 302 has been clipped over a target tissue as desired, a predetermined proximal force may be applied to the sliding component 384 via the control member 312. Once the predetermined proximal force has been applied the cutting edge 396 cuts/shears the shear tabs 388 away from a remaining portion of the interior component 386, as shown in FIG. 15. Upon shearing of the shear tabs 388, the sliding component 384 is permitted to slide proximally relative to the interior component 386 and thereby the clip arms 304 and the capsule 306, until the fingers 394 abut the stop shoulders 390 preventing further proximal motion of the sliding component 384 relative to the interior component 386. Although shearing of the shear tabs 388 result in shed parts, any shed parts will remain trapped in the deployed clip 302.

In the unlocked configuration, the pair of sliding arms 394 are positioned between locking tabs 330 of the capsule 306, so that the inwardly biased locking tabs are deformed radially outward. In the locked configuration, in which the fingers 394 abut the stop shoulders 390, however, the distal end 398 of the sliding arms are moved proximally past the locking tabs 330 so that the locking tabs 330 revert to their inwardly biased configuration. The locking tabs 330 thus engage the distal end 398 of the sliding arms 394 to prevent sliding component 384 from being allowed to move distally relative to the interior component 386, and thereby the clip arms 304 and the capsule 306, to lock the clip 302 in the closed configuration. In this locked configuration, the sliding arms 392 also engage inwardly crimped tabs 328 at a proximal end 322 of the capsule 306, to move the tabs 328 radially outward out of engagement with a proximal portion 316 of device 300 to deploy the clip 302. It will be understood by those of skill in the art that the clipping device 300 may be utilized in a manner substantially similar to the clipping devices 100, 200, to clip the clip 302 over the target tissue and subsequently lock and deploy the clip 302, as described above with respect to the devices 100, 200.

It will be apparent to those skilled in the art that various modifications may be made in the present disclosure, without departing from the scope of the disclosure.

What is claimed is:

1. A clipping device, comprising:
a clip including a capsule extending longitudinally from a proximal end to a distal end and including a channel extending therethrough, and a pair of clip arms, proximal ends of which are slidably received within the channel to move the clip arms between an open configuration and a closed configuration, each of the pair of clip arms including an elongated opening extending through the proximal ends thereof;
a connector including a central portion receivable between the proximal ends of the clip arms and a pin extending from the central portion receivable within the opening of each of the clip arms, the connector movable from an unlocked configuration, in which the pin is received within a distal portion of the elongated opening, to a locked configuration, in which the pin is received within a proximal portion of the elongated opening, when a predetermined force is applied thereto; and
a control member extending through a proximal portion of the clipping device from a proximal end to a distal end releasably coupled to the connector so that a longitudinal movement of the control member relative to the capsule moves the clip between the open and the closed configurations, when the connector is in unlocked configuration.

2. The clipping device of claim 1, wherein the capsule includes a locking tab biased to extend radially into the channel so that, when the pin is moved from the distal portion of the elongated opening to the proximal portion of the elongated opening, the pin is moved proximally past the locking tab until the pin engages the locking tab to lock the clip in the closed configuration.

3. The clipping device of claim 1, wherein the distal and proximal portions of the elongated opening are connected via a middle portion having a width smaller than a width of the distal and proximal portions so that one of the pin and a portion of the clip arms deforms to permit movement of the pin from the distal portion to the proximal portion.

4. The clipping device of claim 3, wherein each of the clip arms include a slit extending from a proximal-most end of the clip arms to the elongated opening to define a pair of fingers that deform by spreading relative to one another to permit movement of the pin proximally past the middle portion.

5. The clipping device of claim 1, wherein the connector includes an overhang extending from the pin to engage an exterior surface of each of the clip arms.

6. The clipping device of claim 1, wherein the central portion of the connector is sized and shaped so that, when the connector is moved from the unlocked configuration to the locked configuration, the central portion moves inwardly crimped tabs at the proximal end of the capsule radially outward, releasing the clip from the proximal portion of the clipping device.

7. The clipping device of claim 1, wherein the connector is connected to the control member via one of a weld, crimped portion and ball tip of the control member that is configured to separate when a predetermined force greater than the predetermine force for moving the connector from the unlocked configuration to the locked configuration is applied thereto.

8. A clipping device, comprising:
a clip including a capsule extending longitudinally from a proximal end to a distal end and including a channel extending therethrough, and a pair of clip arms, proximal ends of which are slidably received within the channel to move the clip arms between an open configuration and a closed configuration, each of the pair of clip arms including an opening extending through the proximal ends thereof;
a connector including a central portion receivable between the proximal ends of the clip arms and a pin extending from the central portion receivable within the opening of each of the clip arms, at least a portion of the central portion configured to be movable relative to the pin and the clip arms from an unlocked configuration to a locked configuration, when a predetermined force is applied thereto; and
a control member extending through a proximal portion of the clipping device from a proximal end to a distal end releasably coupled to the connector so that a longitudinal movement of the control member relative to the capsule moves the clip between the open and the closed configurations, when the connector is in unlocked configuration.

9. The clipping device of claim 8, wherein the capsule includes a locking tab biased to extend radially into the channel so that, when the central portion is moved from the unlocked configuration to the locked configuration, a portion of the central portion engages the locking tab to lock the clip in the closed configuration.

10. The clipping device of claim 8, wherein the central portion includes an elongated opening extending therethrough, the pin received within the elongated opening and movable relative thereto from a proximal portion of the elongated opening in the unlocked configuration to a distal portion of the elongated opening in the locked configuration.

11. The clipping device of claim 10, wherein the proximal and distal portions of the elongated opening are connected to one another via a middle portion having a width smaller than a width of the proximal and distal portions of the elongated opening, so that the pin deformed to permit movement from the proximal portion to the distal portion of the elongated opening.

12. The clipping device of claim 8, wherein the central portion includes an interior member from which the pin extends and a sliding member connected to the interior member via shear tabs that are configured to be sheared off when subject to the predetermined force to move the sliding member from the unlocked configuration to the locked configuration.

13. The clipping device of claim 12, wherein the sliding member includes a pair of sliding arms extending along opposing sides of the interior member, inwardly extending fingers at distal ends of the sliding arms engaging shear tabs at a distal end of the interior member.

14. The clipping device of claim 8, wherein the pin engages the opening of each of the clip arms via one of a friction fit, a weld, an adhesive, and an overhang extending from the pin.

15. The clipping device of claim 8, wherein the central portion of the connector is sized and shaped so that, when the connector is moved from the unlocked configuration to the locked configuration, the central portion engages inwardly crimped tabs at the proximal end of the capsule to move the crimped tabs radially outward, releasing the clip from the proximal portion of the clipping device.

16. A method for clipping tissue, comprising:
inserting a clip device through a working channel of an endoscope to a target site within a body until a clip of the clip device extends distally past a distal end of the working channel, the clip device including a capsule and a pair of clip arms slidably received therein;
moving the clip device between an open configuration, in which distal ends of the clip arms are separated from one another, and a closed configuration, in which the distal ends of the clip arms are drawn toward one another, using a control wire coupled to the clip arms until target tissue is received between the distal ends as desired, a distal end of the control wire coupled to proximal ends of the clip arms via a connector including a central portion received between the proximal ends of the clip arms and a pin extending therefrom receivable within an elongated opening extending through proximal ends of each of the clip arms;
drawing the clip arms proximally into the capsule to move the clip toward the closed configuration to grip the target tissue between the clip arms; and
locking the clip in the closed configuration by drawing the control member proximally relative to the capsule until a predetermined force is exerted on the connector, moving the pin from a distal portion of the elongated opening to a proximal portion of the elongated opening so that the pin engages a locking tab biased radially into the channel of the capsule.

17. The method of claim 16, wherein the distal and proximal portions of the elongated opening are connected via a middle portion having a width smaller than a width of the distal and proximal portions so that one of the pin and a portion of the clip arms deforms to permit movement of the pin from the distal portion to the proximal portion.

18. The method of claim 16, wherein, when the connector is moved proximally relative to the clip arms, the central portion of the connector engages inwardly crimped tabs at the proximal end of the capsule to move the crimped tabs radially outward, releasing the clip from the proximal portion of the clipping device.

19. The method of claim 16, applying a further proximal force along the control member once the clip is locked to release the control member from the connector to deploy the clip within the body.

20. The method of claim 19, wherein a predetermined force required for releasing the control member from the connector is greater than the predetermined force required to lock the clip.

* * * * *